United States Patent [19]

Knoche

[11] 4,199,825
[45] Apr. 29, 1980

[54] BREAST PROSTHESIS

[76] Inventor: Bodo Knoche, Hildesheimer Strasse 213 A, 3014 Laatzen 1, Fed. Rep. of Germany

[21] Appl. No.: 841,478

[22] Filed: Oct. 12, 1977

[30] Foreign Application Priority Data

Oct. 12, 1976 [DE] Fed. Rep. of Germany ... 7631795[U]
Oct. 25, 1976 [DE] Fed. Rep. of Germany ... 7633330[U]
Sep. 19, 1977 [DE] Fed. Rep. of Germany ....... 2742140

[51] Int. Cl.² .............................................. A61F 1/00
[52] U.S. Cl. ......................................... 3/36; 128/479; 249/55
[58] Field of Search ...................... 3/36; 128/463, 505, 128/479, 481; 249/55; 264/222, DIG. 30

[56] References Cited

U.S. PATENT DOCUMENTS

| 2,066,503 | 1/1937 | Wiggers | 3/36 |
| 2,482,297 | 9/1949 | Silverman | 3/36 |
| 2,867,818 | 1/1959 | Creamer | 3/36 |
| 3,196,464 | 7/1965 | McKee | 3/36 |
| 4,086,666 | 5/1978 | Vaskys et al. | 128/505 X |

FOREIGN PATENT DOCUMENTS

| 1072358 | 12/1959 | Fed. Rep. of Germany | 3/36 |
| 2435951 | 2/1976 | Fed. Rep. of Germany | 3/36 |
| 2250280 | 5/1975 | France | 3/36 |

Primary Examiner—Clifford D. Crowder
Attorney, Agent, or Firm—Toren, McGeady and Stanger

[57] ABSTRACT

A breast prosthesis is formed in a mold cavity from a soft silicone rubber cross-linked with hardeners. The prosthesis has a convex outwardly facing surface and a concave cup-shaped inwardly facing surface. The outer surface has a nipple and an areola with a passage formed through the nipple between the inwardly facing and outwardly facing surfaces. The prosthesis can be sized to fit into standard brassieres with its edge located inwardly of the adjacent edge of the brassiere. Extending laterally from one side of the prosthesis is a unitary flap for covering the axillary lymph-gland area. Additional flaps may be molded and glued to the base portion of the prosthesis to cover scar areas not covered by the base part.

10 Claims, 12 Drawing Figures

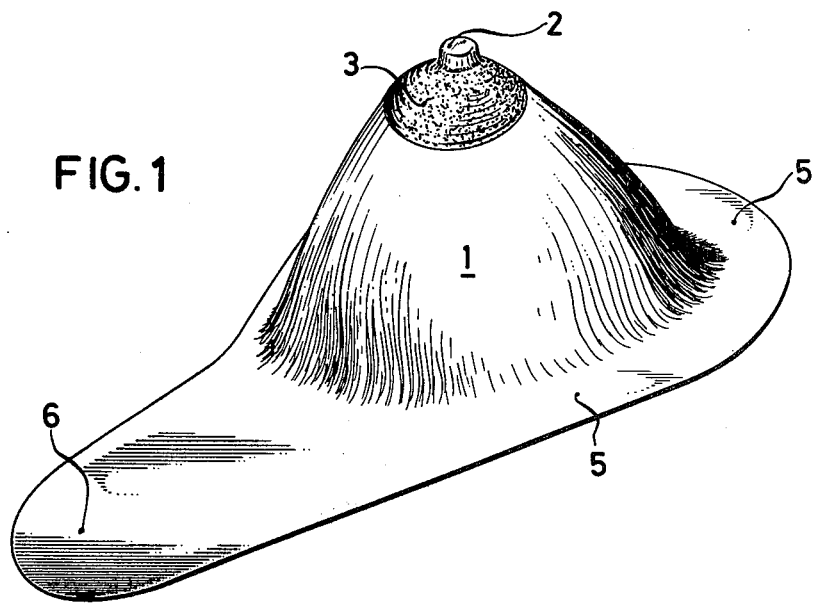
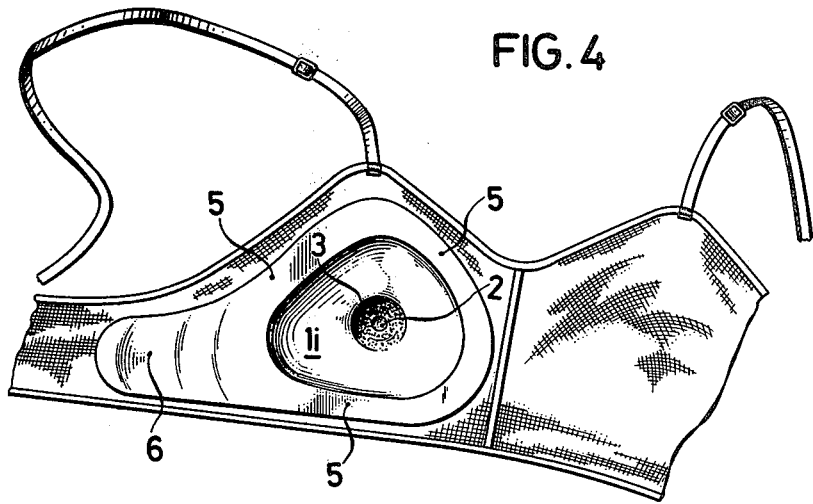

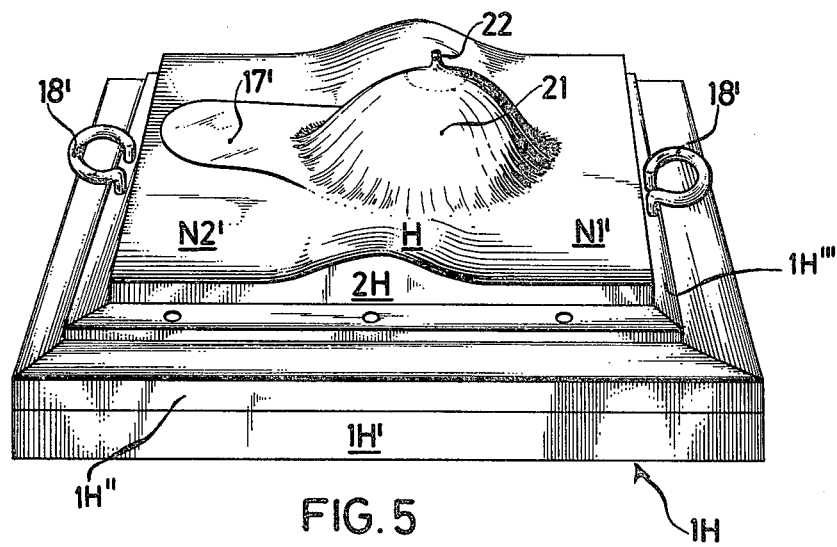
FIG. 5
FIG. 6
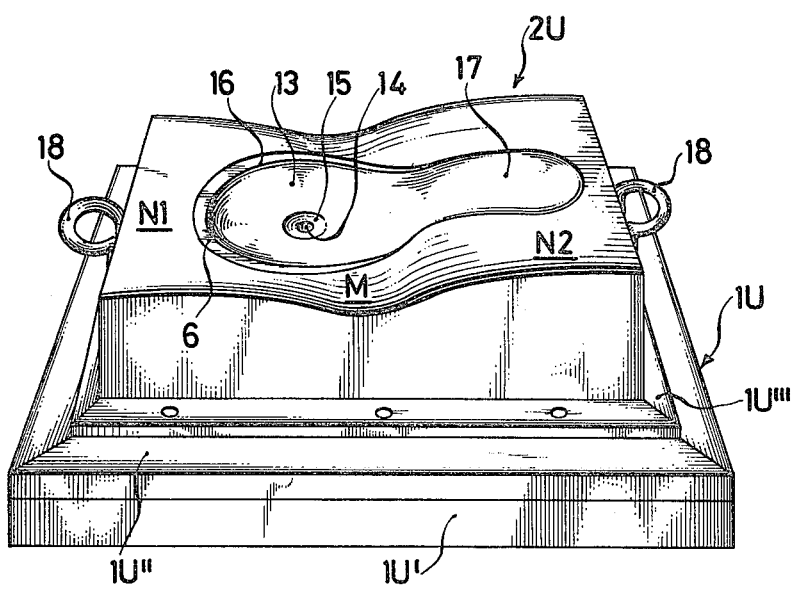

BREAST PROSTHESIS

The invention relates to a breast prosthesis to be used as a replacement in the case of mastectomies, or to provide an optical increase in breast size in the case of women with under-developed breasts. The invention also relates to a method and a mould for producing a prosthesis of this kind.

Breast prostheses made of foam material or of textile material in layers are already known, as are liquid-filled prostheses made of waterproof materials, and receptacles filled with silicone which are used as brassiere fillers.

Known breast prostheses, some of which are very expensive to produce, do not provide a natural-looking replacement breast. They also have the disadvantage that they prevent air from reaching the skin, that they slip easily and may therefore require costly retaining means or sewn-in brassiere cups, and that they differ too greatly from the natural breast, not only in appearance but also in physical properties, particularly in the matters of flexibility and resiliency. This makes itself apparent in the form of deformations embarrassing to the wearer.

It is the purpose of the invention to provide a breast prosthesis having resilient properties as similar as possible to those of the natural breast, which does not affect the skin, which adheres well thereto and therefore does not slip, which is light and airy to wear, which fits into conventional brassieres, and which can therefore be mass-produced economically. Above all, however, the invention is intended to make it possible quite simply to change the shape of the mass-produced prostheses, so that they may be adapted to individual cicatrization.

The invention consists of a breast prosthesis to be inserted or placed in a brassiere, to be produced by die-casting, and to be made of softly resilient, porous, adhesive, skin-coloured synthetic material, e.g. a soft silicone rubber cross-linked with hardeners, the prosthesis consisting of a base having:

(a) a hollow central part pre-arched to the desired depth and width of the brassiere cup, the convex outer surface being in the form of a female breast with a nipple and an areola, while the concave inner surface is arched in the form of a breast while maintaining the desired prosthesis wall-thickness, and has a passage through the center of the nipple; and (b) having thin flexible marginal extensions surrounding the central part, the width thereof being somewhat less than the brassiere edge-strips surrounding the cup, one lateral edge part having an extension, the length and width of which are such that it covers the axillary lymph-gland area when the prosthesis is fitted.

Another characteristic of the invention is the red fibres mixed into the skin-coloured synthetic material.

According to the invention, the base part of the prosthesis is produced in a two-piece mould, the casting surfaces of which are made with material containing aluminum, for example a mixture of synthetic materials and aluminum, the mould consisting of the following parts:

(a) a lower part having a breast-shaped depression at the bottom of which are recesses in the form of the nipple and areola, and having a flat marginal depression which is extended laterally on the shoulder side to form a flap of suitable length and width to cover the axillary lymph-gland area, and (b) an upper part having a breast-shaped protruding arch which fits, when the upper and lower parts of the mould are placed together, into the breast-shaped depression in the lower part, leaving a cavity corresponding to the desired thickness of the prosthesis; in the vicinity of the center of the nipple, the cavity may have a preferably conical pin, the length of which corresponds to the thickness of the prosthesis in this area, and a hollow threaded pin for venting the mould and for the admission of compressed air.

The upper part may also have a depression corresponding in shape, location, and dimensions to the lateral flap depression in the lower part.

In order to be able to produce the base part of the prosthesis in sizes corresponding to standard brassiere and brassiere-cup sizes, the width and depth of the breast-shaped depression in the lower part corresponds to a standard size of brassiere and brassiere cup. Adaptation to current brassiere makes can also be achieved by making the width of the edge and extension depressions correspond to the width of the edge-parts of the cups and the side parts of a particular make of brassiere.

The base part of the prosthesis is made by pouring a liquid synthetic material, such as a silicone rubber cross-linked with hardeners, into the depressions in the lower part of the mould, by placing the upper part of the mould on the lower part in a manner such that the protruding breast-shaped arch projects into the area provided in the breast-shaped depression and, while the synthetic material is still fluid, by applying pressure to the upper and lower parts of the mould, by allowing the synthetic compound to solidify, releasing the solidified casting from the mould, possibly by venting the mould with compressed air, and cutting the flash from the casting.

In order to make it possible to adapt the shape of the prosthesis to individual cicatrization, additional pieces made of the same material as the base part of the prosthesis are provided, and these are, or may be glued to the inner surface of the said base part, preferably at the edges thereof, by means of a special cold-vulcanizing adhesive, the said additional pieces being so shaped, or to be shaped, that they extend the shape of the base part of the prosthesis in accordance with individual cicatrization.

The invention is explained hereinafter in conjunction with the drawings attached hereto, wherein:

FIG. 1 is a diagrammatic representation of the base part of a breast prosthesis according to the invention;

FIG. 4 is a partial diagrammatic representation of a brassiere with the base part of the breast prosthesis placed therein;

FIG. 5 is a diagrammatic representation of the upper part of the mould;

FIG. 6 is a diagrammatic representation of the lower part of the mould used to produce the base part of the prosthesis;

Figure 2:
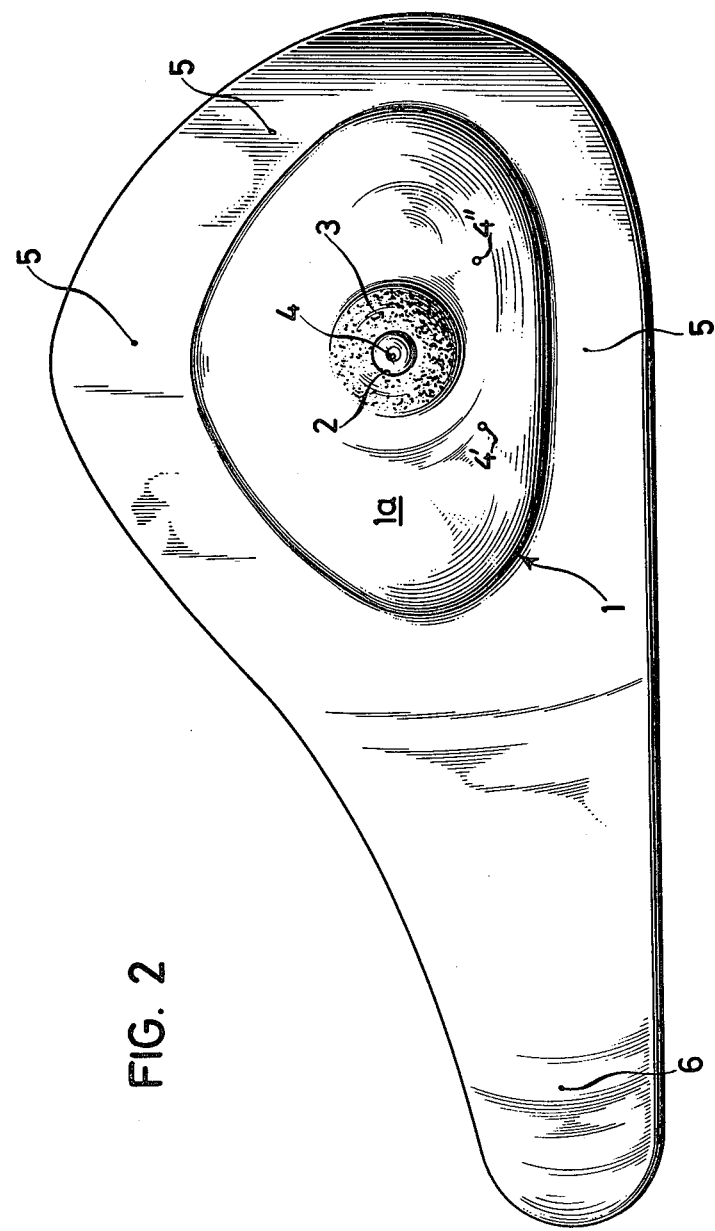
FIG. 2 is a plan view of the front.
Figure 3:
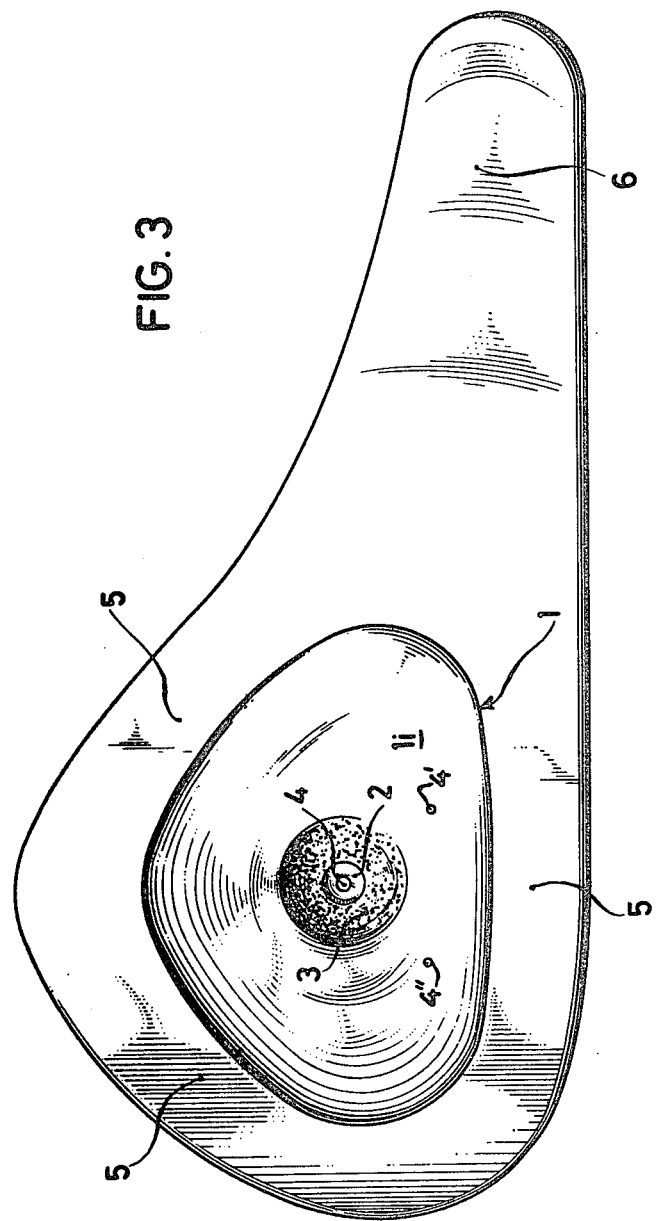
FIG. 3 is a plan view of the back of the base part.

The base part of the prosthesis, made of a soft silicone-rubber compound, consists of a central part 1, of which the convex outer part 1a is in the form of a female breast with a nipple 2 and an areola 3, whereas the concave inner surface 1*i* is arched in the form of a breast. When the prosthesis is used for the optical enlargment of an underdeveloped breast, it may lie upon the breast without depressing it. The distance between outer surface 1*a* and inner surface 1*i* determines the wall-thickness of the prosthesis. Nipple 2 contains a passage 4 (FIGS. 2, 3) which is arranged centrally and which allows air to pass, so that central part 1 of the prosthesis immediately returns to its predetermined shape after being depressed or compressed. Additional passages 4' and 4'' may be provided, preferably on each side of, and below the nipple.

Adjoining central part 1 is a thin, flexible edge 5 which surrounds it in the form of an extension and which is prolonged, on the shoulder side of the prosthesis, to form a part 6, the length and width of which are such that it can cover the axillary lymph-gland area or the scar area itself, in the case of women who have had lymph-gland operations. Edge 5 and extension 6 also enlarge the area of the prosthesis bearing against the skin, thus improving the adhesion thereto.

The dimensions of the prosthesis are governed by those of the make and size of brassiere for which the prosthesis is intended. Prosthesis base parts may be mass-produced in standard brassiere and cup sizes, preferably cup-size B. Thus the protruding arch and width of central part 1 is predetermined, on the one hand, by the particular brassiere-cup size and, on the other hand, as far as the outline of the central part is concerned, by the make of brassiere for which the prosthesis is intended. The width of edge parts 5,6 is such that it is somewhat less than the predetermined width of the edge parts of the brassiere adjoining the cups. As may be gathered from FIG. 4, the base part of the prosthesis is a good fit in the brassiere for which it is intended, and the edges of the prosthesis do not project laterally out of the brassiere.

The material from which the prosthesis is made, namely silicone-rubber cross-linked with hardeners, looks and feels like skin when it is in the hardened condition. It is compatible, even with irradiated skin, and has a slightly adhering suction action, so that it adheres well to the skin. Its weight and resiliency are so similar to natural tissue that the prosthesis may have a slight natural jiggle. The prosthesis adapts well to the body, conducts bodily heat, is strong and easy to care for. The material can be cut or ground, so that custom prosthesis may be made from mass-produced prostheses by cutting and grinding.

The lower part of the mould illustrated in FIG. 6 has a base 1U which may be made of wood, chipboard, or some other suitable material. It consists of a rectangular baseplate 1U' to which are fitted two rectangular frames 1U'' and 1U'''. The rectangular recess in frame 1U'' is smaller than the outline of mould block 2U resting upon it, whereas the the central rectangular recess in frame 1U''' corresponds to the periphery of mould block 2U and forms a frame for mould block 2U inserted into base 1U.

In one simplified design, base 1U may be omitted.

Block 2U is the actual mould. In the example of embodiment illustrated, its ground plan is rectangular, but it may also have any other suitable ground plan. It is made of aluminum or of a synthetic mixture mixed with aluminum. It has a breast-shaped depression 13, at the bottom of which is located a nipple-shaped depression 14 surrounded by an areola-shaped depression 15. The width, depth and shape of depression 13 correspond to the desired external shape of the prosthesis and, in this connection, it is desirable to use standard brassiere and cup sizes. The circumference of depression 13 merges into a flat edge-depression 16 which forms, at the edge of depression 13 near the shoulder, a prolonged extension 17, the length and width of which are such that it may be used to form an extension flap which, when the prosthesis is in place, can cover the axillary lymph-gland area and thus any scars in that area arising from lymph-gland operations. The casting surface of the lower part of the mould undulates, having a pronounced trough M on the shoulder side of the breast depression. This trough slopes gently up to level N1 which is inclined slightly towards the centre of the depression. The slope up to higher level N2 of extension 17 is steeper, and this level also slopes slightly towards depression 13. Handles 18 are used to lift mould block 2U out of base 1U.

The upper part of the mould illustrated in FIG. 5 also consists of a base 1H and a mould block 2H. The design of base 1H, consisting of baseplate 1H' and frames 1H'' and 1H''', corresponds to that of base 1U of the lower part of the mould. Block 2H is made of the same material as block 2U, and it has a breast-shaped protrusion 21, the height and circumference of which are smaller than those of depression 13 in the lower part of the mould by amounts corresponding to the desired thickness of the prosthesis to be cast. Thus when the upper and lower parts of the mould are placed together (FIG. 7), protrusion 21 fits into depression 13 leaving a cavity corresponding to the thickness of the prosthesis. In the nipple area, protrusion 21 is fitted with a conical pin 22, the length of which corresponds to the thickness of the prosthesis, and thus forms, during casting, a passage opening into the nipple. The upper part also has a depression 17' corresponding in position, shape and size to extension 17 in the lower part of the mould. The shape of the surface of the upper part also corresponds to that of the lower part, but the undulation is reversed, so that trough M matches protrusion H, level N1 sloping towards the middle corresponds to a higher level N1' sloping slightly towards the edge of the block, while higher level N2, sloping slightly towards the middle of the block corresponds to lower level N2' sloping slightly towards the edge of the block. Two handles 18' are fitted at locations on the upper part corresponding to those of handles 18 on the lower part of the mould.

Pin 22 may also be omitted, in which case vent-hole 4, and additional passages 4' and 4'', are punched out of the cast base part of the prosthesis.

Figure 7:
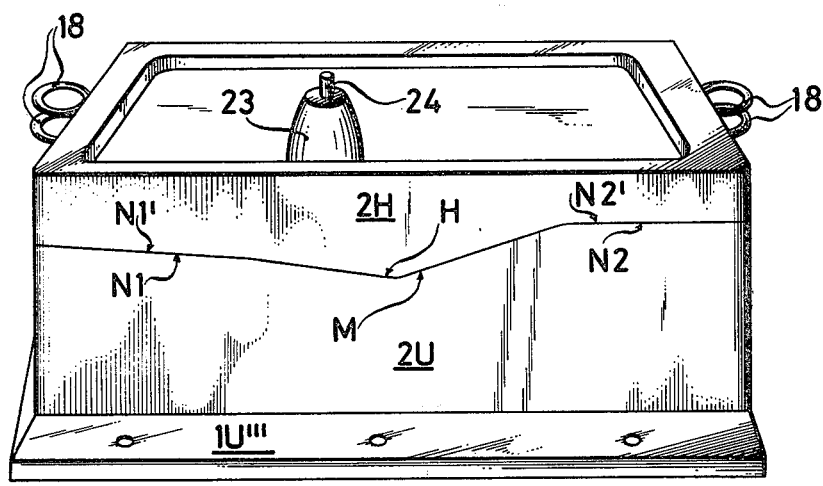
FIG. 7 is a diagrammatic representation of the assembled mould.

As may be gathered from FIG. 7, which shows block 2H removed from base 1H in the "operative" position on the lower part, a tower-like protrusion 23 may be located on the back of block 2H into which is screwed a threaded pin 24 which passes through the entire thickness of block 2H and may be used to introduce compressed air.

In producing the base part of a prosthesis according to the invention, a liquid silicone rubber, cross-linked with hardeners, is poured into the depressions in lower part 2U of the mould. Block 2H is then lifted, by handles 18', out of base 1H and is placed upon block 2U with the edges aligned, protrusion 21 entering into depression 13 on part 2U of the mould. In the positions of parts 1U, 2U and 2H shown in FIG. 7, the silicon rubber is allowed to harden. After possible venting of the mould by means of compressed air introduced through pin 24, block 2H is lifted from block 2U, and the prosthesis blank is removed from the mould, being trimmed or ground if necessary, especially at the edges.

In order to be able to adapt the mould for mass-produced prosthesis base parts to individual cicatrization in the case of mastectomies, additional pieces are provided, and these may also be mass-produced as standard parts, as shown in FIGS. 8a, 8b, 9a, 9b. These additional parts are made of the same material as the prosthesis base parts and are, of course, of the same colour. They are intended to be glued to the inner surface of the said base part, preferably to the edge, by means of a special cold-vulcanizing adhesive, where scars may extend beyond the part of the body covered by the the said base part. The shape of the flap-like additional pieces is such that the parts thereof extending beyond the base part cover the scar area not covered by the said base part. This shaping may be obtained by trimming and grinding additional pieces produced in predetermined sizes and shapes by a unit-construction system.

Figure 8A:
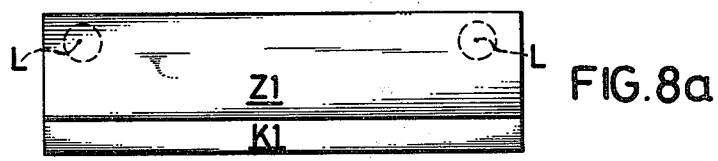
FIGS. 8a, 8b, 9a, 9b illustrate pieces additional to the base part of the prosthesis.
Figure 8B:
Figure 9A:
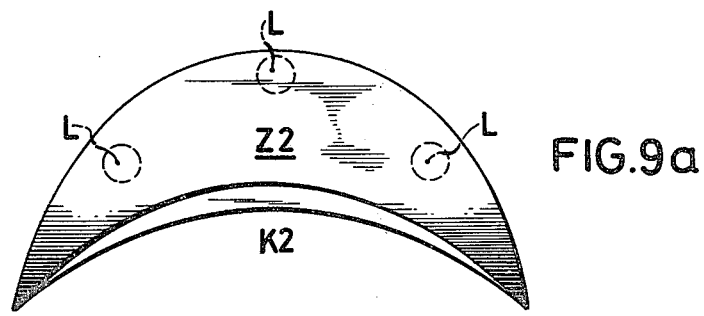
Figure 9B:
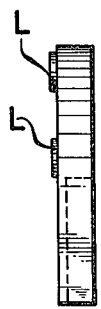

FIGS. 8a, 8b, 9a, 9b show examples of embodiment of additional pieces adapted to be mass-produced in predetermined sizes and shapes, FIG. 8a showing a rectangular, flap-like piece Z1 in plan view and in side elevation (8b), while FIGS. 9a, 9b show a sickle-shaped, flap-like piece 22 in plan view (9a) and in side elevation (9b). Adhesive edges K1 and K2 of pieces Z1 and Z2 are formed by a stepped depression in their upper edges along one edge, a longitudinal edge in the case of the rectangular piece and a concave edge in the case of the sickle-shaped piece.

Recessed adhesive edges K1, K2 of the additional pieces are pushed under the edge of the base part of the prosthesis until these edges abut against the step in the additional piece. According to the shape of the edge area of the base part adjoining a scar area to be covered, an additional piece having a straight or a curved adhesive edge is chosen. After the piece has been glued to the base part, the latter is cut or ground to the desired shape.

Figure 10:
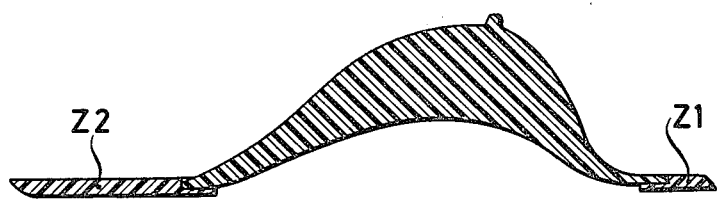
FIG. 10 is a cross section through the base part of a prosthesis, with additional pieces glued thereto.

FIG. 10 is a cross section through a customized prosthesis consisting of a mass-produced base part and mass-produced additional pieces 21 and 22 glued thereto.

The prosthessis may be glued to the body by means of a special cold-vulcanizing adhesive. To this end, preferably round pieces of leather are, or may be, glued with their rough surfaces to the underside of the base part and of the additional pieces, using the same special adhesive. The smooth side of the leather L faces outwardly and may be glued to the body by means of the adhesive.

I claim:

1. A breast prosthesis die cast and formed of a skin-colored soft silicone rubber cross-linked with an amount of hardeners such that it vulcanizes to a soft elastic material forming a prosthesis having an outer surface facing outwardly away from a wearer and an inner surface facing inwardly toward the wearer, and comprising an integral base including a central part, an edge extension and a flap-like section, said central part having a convex outer surface and a concave inner surface providing a hollow cup-shaped form, said convex outer surface having the shape of a female breast including a nipple and an areola, said concave inner surface having a breast-like shape and being spaced from the outer surface providing therebetween the wall thickness of the central part, and said central part having a passage through said nipple extending from the outer surface to said inner surface, said edge extension being thin and flexible and laterally enclosing said central part, said edge extension having a width outwardly from said central part so that said edge extension does not extend outwardly from the edge of a brassiere with which it is worn, said flap-like section connected to said edge extension and extending laterally outwardly from said central part toward the closer side of the wearer with said flap-like section having a length and width sufficient for covering the axillary lymph-gland area when the prosthesis is in place.

2. A breast prosthesis, as set forth in claim 1, wherein red fibers are mixed with said soft silicone rubber.

3. A breast prosthesis, as set forth in claim 1, wherein at least one additional passage is formed between the inner and outer surface of said central part under said areola.

4. A breast prosthesis, as set forth in claim 1, wherein additional passages are formed between the inner and outer surfaces of said central part under and laterally of said areola.

5. A breast prosthesis, as set forth in claim 1, wherein at least one additional part is attached to the inner surface of said edge extension and extends laterally outwardly from said edge extension thereof for covering individual cicatrization.

6. A breast prosthesis, as set forth in claim 5, wherein a cold-vulcanizing adhesive secures said at least one additional part of said edge extension.

7. A breast prosthesis, as set forth in claim 5, wherein at least one additional part comprises a rectangular flap having a longitudinally extending edge for attachment to said edge extension.

8. A breast prosthesis, as set forth in claim 5, wherein said at least one additional part has a longitudinally extending attachment edge and said attachment edge has a stepped depression formed therealong.

9. A breast prosthesis, as set forth in claim 1, wherein said at least one additional part comprises a sickle-shaped flap having a concavely shaped edge for attachment to said edge extension.

10. A breast prosthesis, as set forth in claim 1, wherein at least one piece of leather having a smooth surface on one side and a rough surface on the other side with the rough surface thereof being glued to the inner surface of said edge extension.

* * * * *